United States Patent
Houser et al.

(10) Patent No.: US 8,444,663 B2
(45) Date of Patent: May 21, 2013

(54) ULTRASONIC SURGICAL SHEARS AND TISSUE PAD FOR SAME

(75) Inventors: Kevin L. Houser, Springboro, OH (US); Sarah A. Noschang, Mason, OH (US); Steven Neuenfeldt, Cincinnati, OH (US); Craig N. Faller, Milford, OH (US); Jeffrey J. Vaitekunas, Lakeville, MN (US)

(73) Assignee: Ethicon Endo-Surgery, inc., Cincinnati, OH (US)

( * ) Notice: Subject to any disclaimer, the term of this patent is extended or adjusted under 35 U.S.C. 154(b) by 344 days.

(21) Appl. No.: 12/357,846

(22) Filed: Jan. 22, 2009

(65) Prior Publication Data
US 2010/0023044 A1    Jan. 28, 2010

Related U.S. Application Data

(63) Continuation of application No. 11/065,378, filed on Feb. 24, 2005, now abandoned.

(60) Provisional application No. 60/548,301, filed on Feb. 27, 2004.

(51) Int. Cl.
*A61B 17/32*    (2006.01)

(52) U.S. Cl.
USPC .......................................................... 606/169

(58) Field of Classification Search
USPC .......................................... 606/169, 174, 207
See application file for complete search history.

(56) References Cited

U.S. PATENT DOCUMENTS

| | | | |
|---|---|---|---|
| 3,101,715 A | 8/1963 | Glassman | |
| 3,503,397 A | 3/1970 | Fogarty et al. | |
| 5,322,055 A | 6/1994 | Davison et al. | |
| 6,024,750 A * | 2/2000 | Mastri et al. | 606/169 |

(Continued)

FOREIGN PATENT DOCUMENTS

| | | |
|---|---|---|
| EP | 1433428 | 6/2004 |
| GB | 2348810 A | 10/2000 |
| JP | 10-5236 | 1/1998 |
| JP | 10-127654 | 5/1998 |
| JP | 2000-185052 | 7/2000 |
| WO | WO 98 33437 A1 | 8/1998 |
| WO | WO 2004/012615 A | 2/2004 |

OTHER PUBLICATIONS

Properties of Polyimide (Theromoset unfilled). Datasheet (Online), eFunda Polymer [retrieved on Feb. 26, 2007] Retrieved from the internet; <URL://http://www.efunda.com/materials/polymers/properties/polymer_datasheet.cfm?MajorID=PI&MinorID=7>.

(Continued)

*Primary Examiner* — Ryan Severson
(74) *Attorney, Agent, or Firm* — Verne E. Kreger, Jr.

(57) ABSTRACT

An ultrasonic-surgical-shears tissue pad has a tissue-pad body including a base material and at least one filler material. An alternate ultrasonic-surgical-shears tissue pad has a tissue-pad body having adjoining first and second regions, wherein the first region includes a first material and wherein the second region includes a second material. An ultrasonic surgical shears includes an ultrasonic surgical blade and a clamping arm which is operable to open and close toward the blade and which has a transversely and resiliently flexible distal tip. An alternate ultrasonic surgical shears includes an ultrasonic surgical blade, a clamping arm operable to open and close toward the blade, and a tissue pad attached to the clamping arm and having a clamping surface, wherein at least a portion of the tissue pad is resiliently flexible in a direction substantially perpendicular to the clamping surface.

9 Claims, 3 Drawing Sheets

U.S. PATENT DOCUMENTS

| | | | |
|---|---|---|---|
| 6,102,909 A | * | 8/2000 | Chen et al. .................. 606/45 |
| 6,129,735 A | | 10/2000 | Okada et al. |
| 6,139,561 A | | 10/2000 | Shibata et al. |
| 6,312,430 B1 | | 11/2001 | Wilson et al. |
| 6,325,811 B1 | | 12/2001 | Messerly |
| 6,468,286 B2 | | 10/2002 | Mastri et al. |
| 2002/0128645 A1 | | 9/2002 | Messerly |
| 2003/0114874 A1 | | 6/2003 | Craig et al. |
| 2003/0171747 A1 | | 9/2003 | Kanehira et al. |

OTHER PUBLICATIONS

Dupont Kevlar® 149 Fiber, diam. 12 um. Material Data Sheet [Online] MatWeb, [retrieved on Feb. 26, 2007] Retrieved from the internet: <URL: http://www.matweb.com/search/SpecificMaterialPring.asp?bassnum=PCF003.

Fluoropolymer Comparison—Typical Properties. Comparison Chart [Online]. Dupont [retrieved on Feb. 26, 2007] Retrieved from the internet http://www2.dupont.com/Teflon_Industrial/en_US/tech_info/techinfo_compare.html.

McCarus, Steven D., MD; Physiologic Mechanism of the Ultrasonically Activated Scalpel; Journal of the American Association of Gynecologic Laparoscopists; Aug. 1996; vol. 3, No. 4 601ff.

Feil, Wolgang, MD et al., Ultrasonic Energy for Cutting, Coagulating and Dissecting; p. IV, 17, 21, 23; Theime; Stuttgart-New York ISBN 3-13-127521-9.

European Search Report dated Dec. 10, 2009, EP Application No. 05723928.7, PCT/US2005006272.

* cited by examiner

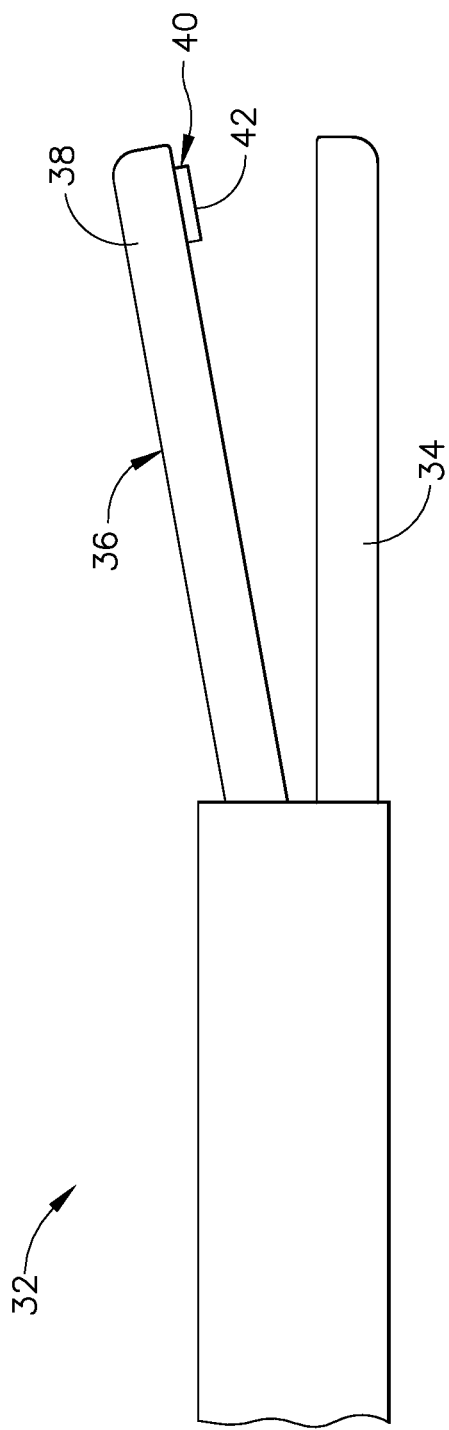
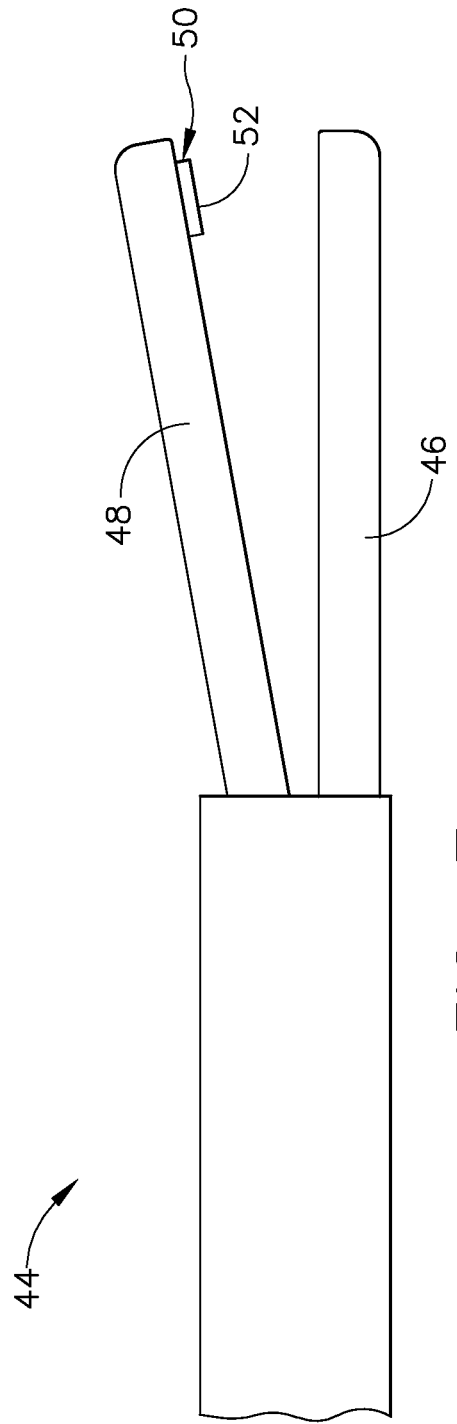

ULTRASONIC SURGICAL SHEARS AND TISSUE PAD FOR SAME

REFERENCE TO RELATED APPLICATIONS

The present application is a continuation of application Ser. No. 11/065,378 filed Feb. 24, 2005 now abandoned which claims the priority benefit of U.S. provisional patent application Ser. No. 60/548,301, filed on Feb. 27, 2004, the contents of which are incorporated herein by reference.

This application contains subject matter related to co-owned patent application No. 60/617,427, filed on Oct. 8, 2004, the contents of which are incorporated herein by reference.

FIELD OF THE INVENTION

The present invention is related generally to surgical instruments, and more particularly to an ultrasonic surgical shears and to a tissue pad for an ultrasonic surgical shears.

BACKGROUND OF THE INVENTION

Ultrasonic surgical instruments are known which include an ultrasonic surgical shears having an ultrasonic surgical blade, a clamping arm operable to open and close toward the blade, and a polytetrafluoroethylene tissue pad which is attached to the clamping arm and which includes a clamping surface. The clamping arm exerts a clamping force on a blood vessel which is positioned between the clamping surface of the tissue pad and the blade. The result of the ultrasonically-vibrating ultrasonic surgical blade and the clamping force on the blood vessel is a coaptation of the blood vessel (a bringing together of the walls of the blood vessel), a transection (a cutting) of the coapted blood vessel, and a coagulation (a sealing) of the coapted cut ends of the blood vessel. At the completion of a tissue transection, the ultrasonically-vibrating ultrasonic surgical blade contacts and cuts away some of the polytetrafluoroethylene tissue pad because of the frictional abrasion and frictional heat generated by the blade vibrating against the tissue pad. Exemplary devices are described in U.S. Pat. Nos. 5,322,055 and 6,325,811, the contents of which are incorporated herein by reference.

Still, scientists and engineers continue to seek improved ultrasonic surgical shears and improved tissue pads for ultrasonic surgical shears.

SUMMARY OF THE INVENTION

A first embodiment of an ultrasonic-surgical-shears tissue pad of the invention includes an ultrasonic-surgical-shears tissue pad body having a base material and at least one filler material which is a different material from the base material.

A second embodiment of an ultrasonic-surgical-shears tissue pad of the invention includes an ultrasonic-surgical-shears tissue pad body having adjoining first and second regions, wherein the first region includes a first material and wherein the second region includes a second material which is a different material from the first material.

A first embodiment of an ultrasonic surgical shears of the invention includes an ultrasonic surgical blade and a clamping arm operable to open and close toward the blade and having a transversely and resiliently flexible distal tip.

A second embodiment of an ultrasonic surgical shears of the invention includes an ultrasonic surgical blade, a clamping arm operable to open and close toward the blade, and a tissue pad attached to the clamping arm and having a clamping surface. At least a portion of the tissue pad is resiliently flexible in a direction substantially perpendicular to the clamping surface.

Several benefits and advantages are obtained from one or more of the embodiments of the invention. Having a tissue pad with a base material and at-least-one filler material allows the base material and the at-least-one filler material to be chosen with a different hardness, stiffness, lubricity, dynamic coefficient of friction, heat transfer coefficient, abradability, heat deflection temperature, and/or melt temperature to improve the wearability of the tissue pad which is important when high clamping forces are employed because tissue pads wear faster at higher clamping forces than at lower clamping forces. Applicants found, in one experiment, that a 15% graphite-filled polytetrafluoroethylene tissue pad showed substantially the same wear with a 7 pound clamping force as a 100% polytetrafluoroethylene tissue pad showed with a 1.5 pound clamping force. Having a flexible clamping arm and/or a flexible tissue pad should also improve the wearability of the tissue pad due to the ability of the flexible member to more evenly distribute the load across the entire surface of the tissue pad.

The present invention has, without limitation, application in straight or curved ultrasonic surgical blades as disclosed in the patents incorporated by reference and further in hand-activated instruments as well as in robotic-assisted instruments.

BRIEF DESCRIPTION OF THE FIGURES

FIG. 6 is a schematic side elevational view of a portion of an embodiment of an ultrasonic surgical shears of the invention;

FIG. 7 is a schematic side elevational view of a portion of an alternate embodiment of an ultrasonic surgical shears of the invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, examples, etc. can be combined with any one or more of the other following-described embodiments, examples, etc.

Figure 1:
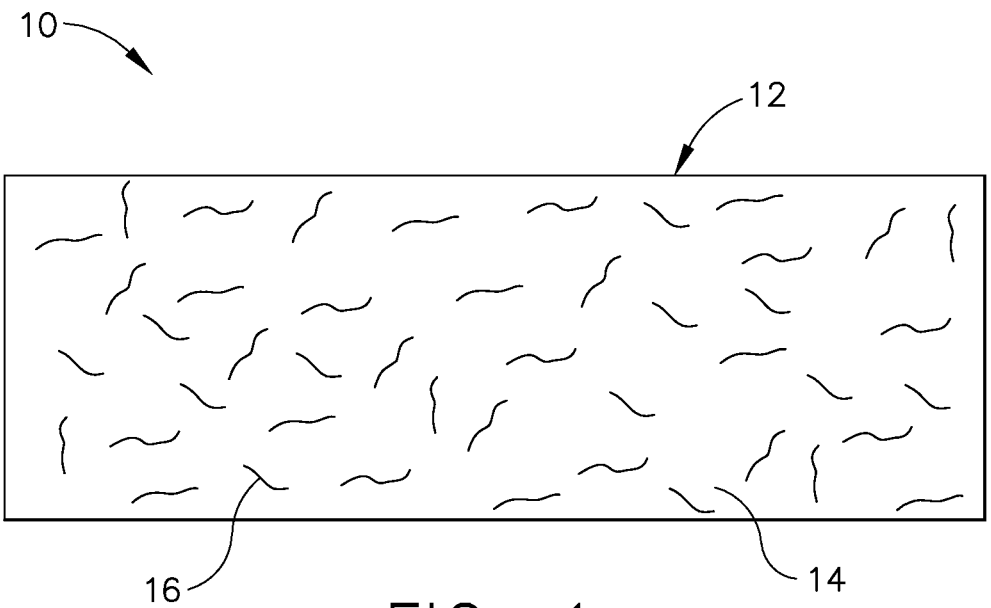
FIG. 1 is a cross-sectional view of a portion of a first embodiment of an ultrasonic-surgical-shears tissue pad of the invention.

Referring now to the Figures, in which like numerals indicate like elements, FIG. 1 illustrates a first embodiment of an ultrasonic-surgical-shears tissue pad 10 of the invention. The ultrasonic-surgical-shears tissue pad 10 has an ultrasonic-surgical-shears tissue pad body 12 including a base material 14 and at least one filler material 16 which is a different material from the base material 14.

In one example of the embodiment of the ultrasonic-surgical-shears tissue pad 10 of FIG. 1, the at-least-one filler material 16 has at least one property which has a different value from that of the at-least-one property of the base material 14, wherein the at-least-one property is chosen from the group consisting of: hardness, stiffness, lubricity, dynamic coefficient of friction, heat transfer coefficient, abradability, heat deflection temperature, and melt temperature. In one variation, at least two or more or all of the properties have different values for the base material 14 and the at-least-one filler material 16.

In one illustration of the ultrasonic-surgical-shears tissue pad 10 of FIG. 1, the base material 14 has a heat deflection temperature greater than 500 degrees Fahrenheit. In the same or a different illustration, the base material 14 has a melt temperature greater than 700 degrees Fahrenheit. In the same or a different illustration, the base material 14 has a dynamic coefficient of friction less than 0.3 at pressure-velocity values greater than 30,000 pounds per foot-second. In one choice of materials of the ultrasonic-surgical-shears tissue pad 10 of FIG. 1, the base material 14 consists essentially of a thermoset plastic material. In one variation, the base material 14 consists essentially of a polyimide material.

In one enablement of the invention, the at-least-one filler material 16 has a hardness which is different than that of the base material 14. In the same or a different enablement, the at-least-one filler material 16 has a stiffness which is different than that of the base material 14. In the same or a different enablement, the at-least-one filler material 16 has a lubricity which is different than that of the base material 14. In the same or a different enablement, the at-least-one filler material 16 has a dynamic coefficient of friction which is different than that of the base material 14. In the same or a different enablement, the at-least-one filler material 16 has a heat transfer coefficient which is different than that of the base material 14. In the same or a different enablement, the at-least-one filler material 16 has an abradability which is different than that of the base material 14. In the same or a different enablement, the at-least-one filler material 16 has a heat deflection temperature which is different than that of the base material 14. In the same or a different enablement, the at-least-one filler material 16 has a melt temperature which is different than that of the base material 14.

In one example of the invention, the at-least-one filler material 16 is chosen from the group consisting of glass, carbon fiber, graphite, metal particles, molybdenum disulfide, a liquid lubricant, a solid material that changes to a more lubricous powder at an increased temperature, a solid that changes to a liquid at an increased temperature, carbon nanotubes, polyphenelene sulfone, polyphenelene sulfide, sumifine powder, boron nitride, polytetrafluoroethylene powder, silicone oil, and an aerogel.

In the same or another example of the invention, the base material 14 is chosen from the group consisting of a plastic, a porous ceramic, a polished ceramic, a self-constructing nanocomposite (a material that is a combination of two or more materials that, when cured, structures itself into a predetermined matrix), a highly crosslinked polytetrafluoroethylene, a metal having a hardness at least as low as tantalum, a fluorinated polyimide, a clay-filled nanocomposite-forming polymer (these are materials that are filled with small amounts of clay material where the clay material combines with the polymer molecule to yield a material with superior properties to the original polymer material such as a clay-filled nylon that exhibits a heat deflection temperature of at least 100 degrees Fahrenheit higher than that of the regular nylon material), and a polyimide material. In one variation, the plastic is chosen from the group consisting of a polytetrafluoroethylene and a polyimide. In one modification, substantially 85% of the ultrasonic-surgical-blade tissue pad body 12 consists essentially of the base material 14 and substantially 15% of the ultrasonic-surgical-blade tissue pad body 12 consists essentially of the at-least-one filler material 16, wherein the base material 14 consists essentially of polytetrafluoroethylene, and wherein the at-least-one filler material 16 consists essentially of graphite.

In one expression of the invention, the ultrasonic-surgical-shears tissue pad body 12 includes a base material 14 and at least one filler material 16, wherein the base material 14 is chosen from the group consisting of a plastic, a porous ceramic, a polished ceramic, a self-constructing nanocomposite, a highly crosslinked polytetrafluoroethylene, a metal having a hardness at least as low as tantalum, a fluorinated polyimide, a clay-filled nanocomposite-forming polymer, and a polyimide material.

In one configuration of the invention, not shown, the ultrasonic-surgical-shears tissue pad body consists essentially of a material chosen from the group consisting of a porous ceramic, a polished ceramic, a self-constructing nanocomposite, a highly crosslinked polytetrafluoroethylene, a metal having a hardness at least as low as tantalum, a fluorinated polyimide, a clay-filled nanocomposite-forming polymer, and a polyimide.

In one deployment of the invention, the ultrasonic-surgical-shears tissue pad body 12 includes a base material 14 and at least one filler material 16, wherein the base material 14 consists essentially of a porous polymer, and wherein the at-least-one filler material 16 is chosen from the group consisting essentially of a solid lubricant, a liquid lubricant, and a solid lubricant which changes to a liquid lubricant at an increased temperature.

In one arrangement of the invention, not shown, the ultrasonic-surgical-shears tissue pad body consists essentially of a porous wicking material which upon contact wicks patient body fluids into the ultrasonic-surgical-shears tissue pad body or absorbs water when immersed in a water containing solution such as saline. These materials improve the temperature performance of the tissue pad body by absorbing some of the heat energy to evaporate the water entrapped in the tissue pad body.

Figure 2:
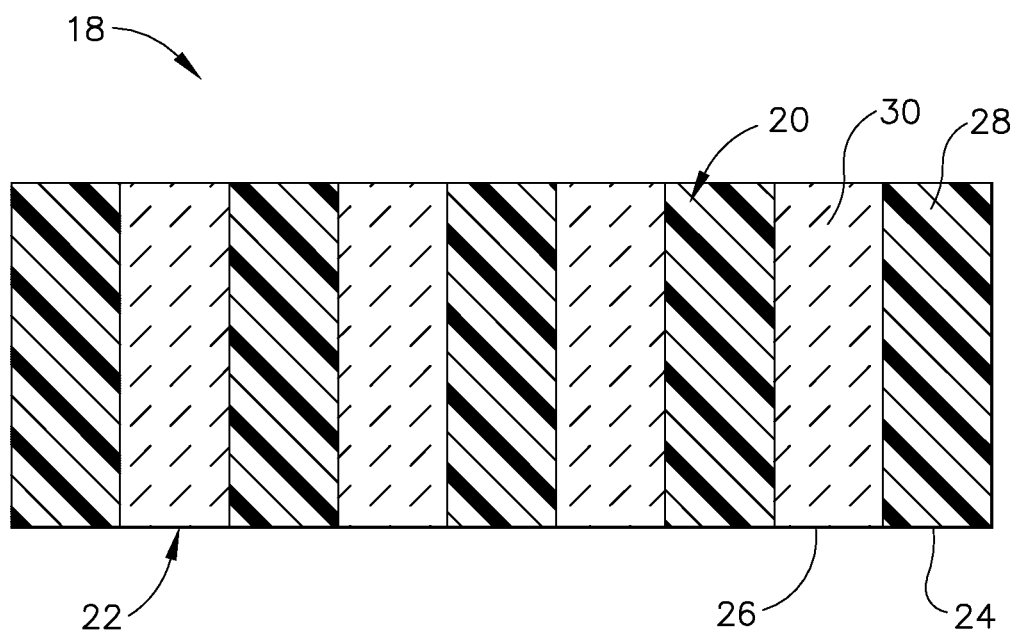
FIG. 2 is a cross-sectional view of a portion of a second embodiment of an ultrasonic-surgical-shears tissue pad of the invention.

FIG. 2 illustrates a second embodiment of an ultrasonic-surgical-shears tissue pad 18 of the invention. The ultrasonic-surgical-shears tissue pad 18 has an ultrasonic-surgical-shears tissue pad body 20 having adjoining first and second regions 24 and 26, wherein the first region 24 includes a first material 28 and wherein the second region 26 includes a second material 30 which is a different material from the first material 28. The above description of the tissue pad 18 of FIG. 2 is equally applicable to the tissue pads of FIGS. 3-5, as can be appreciated by the artisan from the below discussion of the tissue pads of FIGS. 3-5. In one variation of the tissue pad 18 of FIG. 2, the first region 24 consists essentially of the first material 28 and the second region 26 consists essentially of the second material 30. In another variation, the first region 24 includes a base material and at least one filler material, wherein the base material is the first material 28. In the same or a different variation, the second region 26 includes a base material and at least one filler material, wherein the base material is the second material 30.

In one construction of the tissue pad 18 of FIG. 2, the interface between the first and second regions 24 and 26 of the tissue pad body 20 is substantially perpendicular to the clamping surface 22 of the tissue pad body 20 as shown in the figure. In another construction, not shown, the interface between the first and second regions is substantially parallel to the clamping surface (this can be visualized by rotating the tissue pad 18 in FIG. 2 by ninety degrees. In an additional construction, not shown, the interface is slanted with respect to the clamping surface at an angle between substantially 1 and 89 degrees, as can be appreciated by the artisan.

It is noted that the examples, illustrations, choices of materials, etc. described for the embodiment of the ultrasonic-surgical-shears tissue pad 10 of FIG. 1 are equally applicable to the embodiment of the ultrasonic-surgical-shears tissue pad 18 of FIG. 2 with the phrase "first material 28" replacing the phrase "base material 14" and with the phrase "second material 30" replacing the phrase "at-least-one filler material 16".

Figure 3:
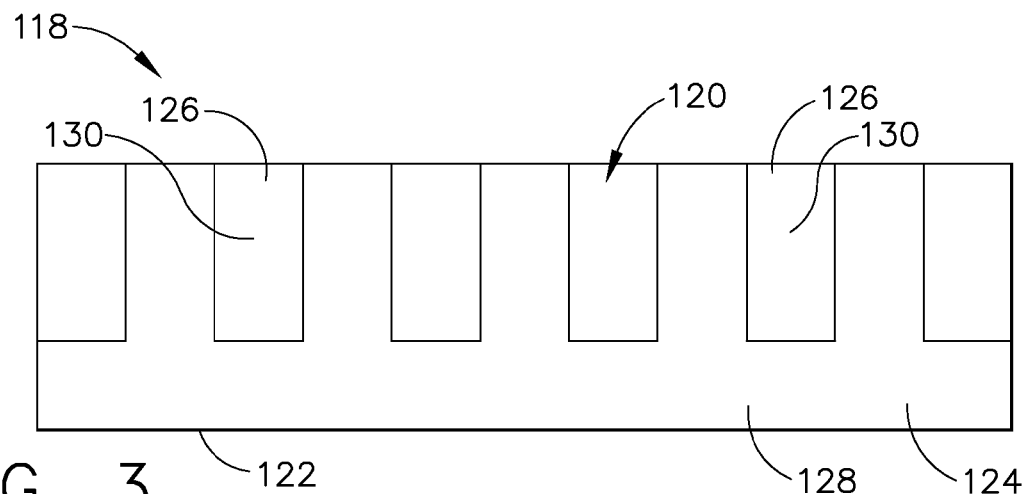
FIG. 3 is a side-elevational view of a first alternate embodiment of the tissue pad of FIG. 2.

FIG. 3 is an exterior side-elevational view of a tissue pad 118 which is a first alternate embodiment to the tissue pad 18 of FIG. 2. Tissue pad 118 includes tissue pad body 120 having adjoining first and second regions 124 and 126 as shown in the figure. First region 124 includes a first material 128, and second region 126 includes a second material 130 which is a different material from the first material. In one variation, the clamping surface 122 of the tissue pad body 120 consists essentially of the first material 128 which extends away from the clamping surface 122 toward the second regions 126. In one enablement, the material transversely between the second regions 126 is the first material 128 of the first region 124. In another enablement, not shown, a third region with a third material is disposed transversely between the second regions.

Figure 4:
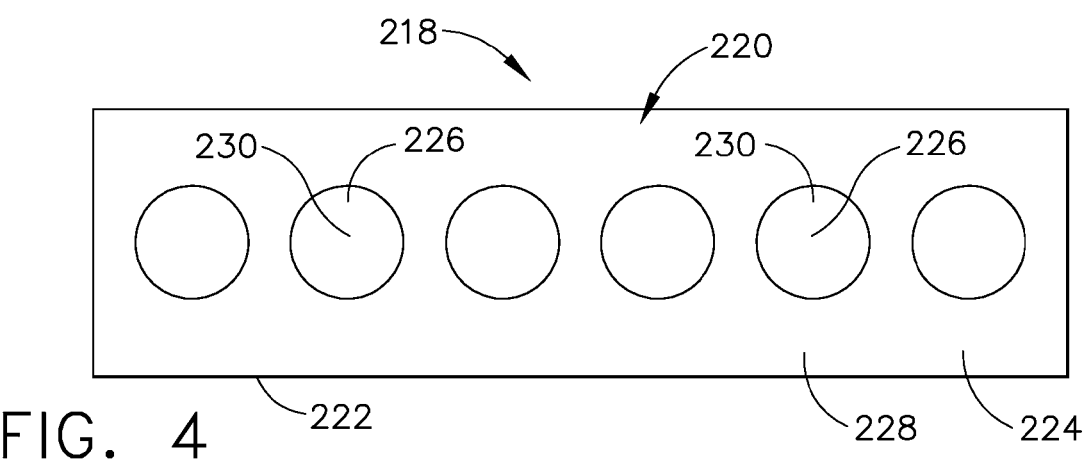
FIG. 4 is a side-elevational view of a second alternate embodiment of the tissue pad of FIG. 2.

FIG. 4 is an exterior side-elevational view of a tissue pad 218 which is a second alternate embodiment to the tissue pad 18 of FIG. 2. Tissue pad 218 includes tissue pad body 220 having adjoining first and second regions 224 and 226 as shown in the figure. First region 224 includes a first material 228, and second region 226 includes a second material 230 which is a different material from the first material. In one variation, the clamping surface 222 of the tissue pad body 220 consists essentially of the first material 228 which extends away from the clamping surface 222 toward the second regions 226. In one enablement, the material transversely between the second regions 226 is the first material 228 of the first region 224. In another enablement, not shown, a third region with a third material is disposed transversely between the second regions.

Figure 5:
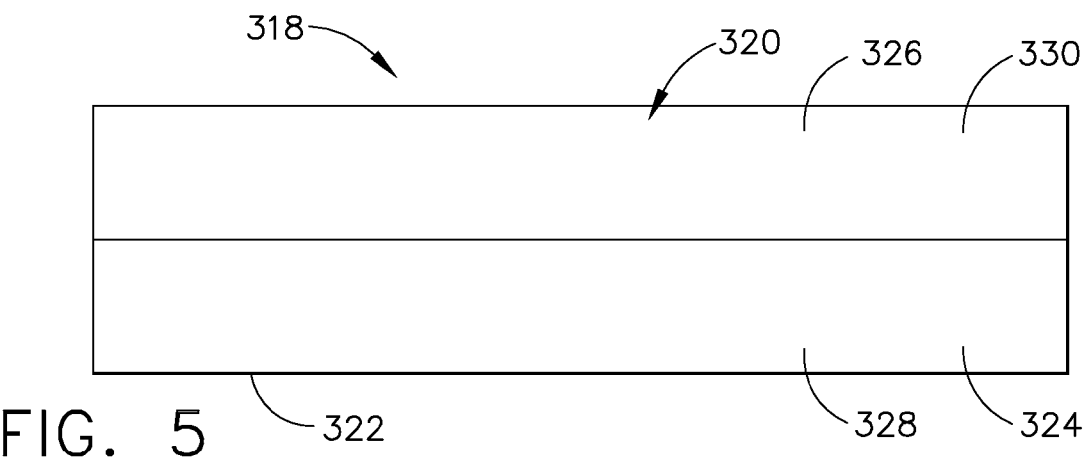
FIG. 5 is a side-elevational view of a third additional alternate embodiment of the tissue pad of FIG. 2.

FIG. 5 is an exterior side-elevational view of a tissue pad 318 which is a third alternate embodiment to the tissue pad 18 of FIG. 2. Tissue pad 318 includes tissue pad body 320 having adjoining first and second regions 324 and 326 as shown in the figure. First region 324 includes a first material 328, and second region 326 includes a second material 330 which is a different material from the first material. In one variation, the clamping surface 322 of the tissue pad body 320 consists essentially of the first material 328 which extends away from the clamping surface 322 toward the second regions 326. In one application, tissue pad 318 improves pad life by the first region 324 being sacrificial and being abraded or melted relatively quickly but having certain properties, such as lubricity, that are desirable. The ultrasonic surgical blade, not shown in FIG. 5, moves through the first material 318 and then comes into contact with the second material 330. The second material 330 is selected for properties that make it abrade or melt less than the first material 318.

It is noted that the examples, illustrations, choices of materials, etc. described for the embodiment of the tissue pad 18 of FIG. 2 are equally applicable to the embodiments of the tissue pad 118, 218 and 318 of FIGS. 3-5. Other alternate embodiments to the tissue pad 18 are left to the artisan.

FIG. 6 illustrates a first embodiment of an ultrasonic surgical shears 32 of the invention. The ultrasonic-surgical-shears 32 includes an ultrasonic surgical blade 34 and a clamping arm 36 operable to open and close toward the blade 34 and having a transversely and resiliently flexible distal tip 38. By "resiliently flexible distal tip" is meant that the distal tip 38 resiliently flexes during clamping of the clamping arm 36 such as when the ultrasonic-surgical-shears 32 is used to transect and seal a blood vessel, disposed between the clamping surface 42 and the ultrasonic surgical blade 34, whose walls have been coapted by a clamping force applied via the clamping arm 36. In one implementation of the first expression, the ultrasonic surgical shears 32 also includes a tissue pad 40 attached to the clamping arm 36 and having a clamping surface 42, wherein the tissue pad 40 is resiliently flexible in a direction substantially perpendicular to the clamping surface 42. In one illustration of the embodiment of the ultrasonic-surgical-shears 32, the tissue pad 40 includes a base material and at least one filler material as previously described for the tissue pad 10 of FIG. 1. In another illustration of the ultrasonic-surgical-shears 32, the tissue pad 40 includes a first material and a second material as previously described for the tissue pad 18, 118, 218 or 318 of FIGS. 2-5.

FIG. 7 illustrates a second embodiment of an ultrasonic surgical shears 44 of the invention. The ultrasonic-surgical-shears 44 includes an ultrasonic surgical blade 46, a clamping arm 48 operable to open and close toward the blade 46, and a tissue pad 50. The tissue pad 50 is attached to the clamping arm 48 and has a clamping surface 52. At least a portion of the tissue pad 50 is resiliently flexible in a direction substantially perpendicular to the clamping surface 52. By "resiliently flexible" is meant that the tissue pad 50 resiliently flexes during clamping of the clamping arm 48 such as when the ultrasonic-surgical-shears 44 is used to transect and seal a blood vessel, disposed between the clamping surface 52 and the ultrasonic surgical blade 46, whose walls have been coapted by a clamping force applied via the clamping arm 48. In one illustration of the embodiment of the ultrasonic-surgical-shears 44, the tissue pad 50 includes a base material and at least one filler material as previously described for the tissue pad 10 of FIG. 1. In another illustration of the ultrasonic-surgical-shears 44, the tissue pad 40 includes a first material and a second material as previously described for the tissue pad 18, 118, 218 or 318 of FIGS. 2-5.

Several benefits and advantages are obtained from one or more of the embodiments of the invention. Having a tissue pad with a base material and at-least-one filler material allows the base material and the at-least-one filler material to be chosen with a different hardness, stiffness, lubricity, dynamic coefficient of friction, heat transfer coefficient, abradability, heat deflection temperature, and/or melt temperature to improve the wearability of the tissue pad which is important when high clamping forces are employed because tissue pads wear faster at higher clamping forces than at lower clamping forces. Applicants found, in one experiment, that a 15% graphite-filled polytetrafluoroethylene tissue pad showed substantially the same wear with a 7 pound clamping force as a 100% polytetrafluoroethylene tissue pad showed with a 1.5 pound clamping force. Having a flexible clamping arm and/or a flexible tissue pad should also improve the wearability of the tissue pad due to the ability of the flexible member to more evenly distribute the load across the entire surface of the tissue pad.

While the present invention has been illustrated by a description of several embodiments, it is not the intention of the applicants to restrict or limit the spirit and scope of the appended claims to such detail. Numerous other variations, changes, and substitutions will occur to those skilled in the art without departing from the scope of the invention. For instance, the ultrasonic surgical shears and the tissue pad of the invention have application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended Claims.

What is claimed is:

1. An ultrasonic-surgical-shears tissue pad comprising: a unitary ultrasonic-surgical-shears tissue pad including a base material, the pad and base material define a first surface and a second surface and wherein the pad further comprises at least one filler material which is a different material from the base material, and dispersed within the base material.

2. The ultrasonic-surgical-shears tissue pad of claim 1, wherein the at-least-one filler material has at least one property which has a different value from that of the at-least-one property of the base material, and wherein the at-least-one property is chosen from the group consisting of: hardness, stiffness, lubricity, dynamic coefficient of friction, heat transfer coefficient, abradability, heat deflection temperature, and melt temperature.

3. The ultrasonic-surgical-shears tissue pad of claim 1, wherein the base material has a heat deflection temperature greater than 500 degrees Fahrenheit.

4. The ultrasonic-surgical-shears tissue pad of claim 1, wherein the base material has a melt temperature greater than 700 degrees Fahrenheit.

5. The ultrasonic-surgical-shears tissue pad of claim 1, wherein the base material has a dynamic coefficient of friction less than 0.3 at pressure-velocity values greater than 30,000 pounds per foot-second.

6. The ultrasonic-surgical-shears tissue pad of claim 1, wherein the base material consists essentially of a thermoset plastic material.

7. The ultrasonic-surgical-shears tissue pad of claim 6, wherein the base material consists essentially of a polyimide material.

8. The ultrasonic-surgical-shears tissue pad of claim 6, wherein the base material consists essentially of polytetrafluoroethylene and the at least one filler material is graphite.

9. The ultrasonic-surgical-shears tissue pad of claim 1, wherein at least a portion of the at-least-one filler material is at least in part coincident to at least a portion of one of the first and second surfaces.

* * * * *